(12) United States Patent
Veronikis

(10) Patent No.: US 9,168,119 B2
(45) Date of Patent: Oct. 27, 2015

(54) SURGICAL SYSTEMS AND METHODS FOR TRANSVAGINAL APICAL SUSPENSION

(76) Inventor: Dionysios Veronikis, Town of Country, MO (US)

(*) Notice: Subject to any disclaimer, the term of this patent is extended or adjusted under 35 U.S.C. 154(b) by 278 days.

(21) Appl. No.: 12/897,368

(22) Filed: Oct. 4, 2010

(65) Prior Publication Data

US 2011/0245588 A1     Oct. 6, 2011

Related U.S. Application Data

(60) Provisional application No. 61/249,511, filed on Oct. 7, 2009.

(51) Int. Cl.
*A61F 2/00* (2006.01)
*A61B 17/00* (2006.01)

(52) U.S. Cl.
CPC .............. *A61F 2/0045* (2013.01); *A61F 2/0063* (2013.01); *A61B 2017/00805* (2013.01)

(58) Field of Classification Search
CPC ................ A61F 2/0045; A61F 2/0063; A61F 2002/0072
USPC .......................... 600/29–31, 37; 606/151–159
See application file for complete search history.

(56) References Cited

U.S. PATENT DOCUMENTS

| | | | |
|---|---|---|---|
| 7,070,556 B2 | 7/2006 | Anderson et al. | |
| 7,357,773 B2 | 4/2008 | Watschke | |
| 7,878,970 B2* | 2/2011 | Goldberg | 600/37 |
| 2003/0220538 A1* | 11/2003 | Jacquetin | 600/37 |
| 2006/0258898 A1* | 11/2006 | Montpetit et al. | 600/30 |
| 2006/0260618 A1* | 11/2006 | Hodroff et al. | 128/830 |
| 2009/0171141 A1* | 7/2009 | Chu | 600/37 |
| 2010/0263674 A1* | 10/2010 | Rane | 128/834 |

FOREIGN PATENT DOCUMENTS

| | | |
|---|---|---|
| WO | 2009017680 | 2/2009 |
| WO | 2009075800 | 6/2009 |

* cited by examiner

*Primary Examiner* — Catherine B Kuhlman
(74) *Attorney, Agent, or Firm* — Inskeep IP Group, Inc.

(57) ABSTRACT

Systems and surgical methods and procedures for performing transvaginal apical suspension are provided.

15 Claims, 4 Drawing Sheets

SURGICAL SYSTEMS AND METHODS FOR TRANSVAGINAL APICAL SUSPENSION

PRIORITY

This application claims the benefit of U.S. Provisional Application Ser. No. 61/249,511 entitled "SURGICAL SYSTEMS AND METHODS FOR TRANSVAGINAL APICAL SUSPENSION," filed Oct. 7, 2009, which application is hereby incorporated by reference in its entirety.

FIELD OF THE INVENTION

The present invention relates to systems and methods for surgical techniques implemented to perform transvaginal apical suspension.

BACKGROUND OF THE INVENTION

Pelvic prolapse, including vaginal prolapse, can be caused by the weakening or breakdown of various parts of the pelvic support system, such as the pelvic floor or tissue surrounding the vagina. Due to the lack of support, structures such as the uterus, rectum, bladder, urethra, small intestine, or vagina, may begin to fall out of their normal positions. Prolapse may cause pelvic discomfort and may affect bodily functions such as urination and defecation. Pelvic prolapse conditions can be treated by various surgical and nonsurgical methods. Nonsurgical treatments for vaginal prolapse include pelvic muscle exercises, estrogen supplementation, and vaginal pessaries. The Perigee® system, developed by American Medical Systems, located in Minnetonka, Minn. ("AMS") is a surgical technique for the repair of anterior vaginal prolapse. Additionally, the Apogee® system, developed by AMS is a surgical technique for the repair of vaginal vault prolapse and posterior prolapse. Further, AMS developed a single-incision technique, the Elevate® system, to treat cystoceles and vault prolapse. The Elevate® system includes a slim needle and low profile self-fixating tips designed to minimize tissue trauma and provide for a shorter recovery period for the patient.

SUMMARY OF THE INVENTION

The present disclosure is generally directed to a surgical procedure and system for transvaginal apical suspension, including:

Dissection—The procedure can start with a posterior dissection featuring an elongated diamond shaped incision that spans the entire vaginal length starting at the perineal body and ending at the vaginal cuff. The dissection first involves separating the vaginal wall from the rectum then shifts to opening up the pararectal space. The dissection is aided by a Martin Arms system which is fixed to the patient's bed and holds both regular and custom made retractors. Once the pararectal space is entered, four fixed retractors hold it open to the depth of 14 cm. At the depth of the retracted space lies anatomical structure surrounding the sacrum (S2-S3).

Fixation—Fixation can utilize a Monarc® (commercial product of American Medical Systems, Inc. of Minnetonka, Minn.) tape. It starts with passing a long custom designed needle through the pelvic sidewall starting with the pubococcygeus muscle. The needle is loaded through an eyelet on its tip with a double looped suture. As the needle traverses the levator plate it emerges at a location deep inside the pararectal tunnel. With another long custom designed needle, the suture on the top of the first needle is fished out and tied to one end on the Monarch mesh tape. The suture is then pulled through the needle pass dragging with it the mesh tape. Fixation of the mesh tape is achieved by pulling the plastic sheath off of the Monarc tape and allowing the Sparc mesh to engage the tissue.

Suspension—Suspension of the vaginal apex can be carried out by attaching one end of the Monarc tape to the vaginal apex at a midline of the cuff. The location of the attachment point could shift posteriorly or anteriorly based on specific conditions in the anterior or posterior vaginal compartments and requirements for maintaining tensioning balance on the vaginal wall between the two compartments. Once the tape is sutured to the apex, the apex is mechanically lifted with packing and the slack that is created in the Monarc tape is taken out by pulling on the mesh tape end that is protruding from the pelvic sidewall and pubococcygeus muscle. To finalize the apical suspension, the sheath covering the mesh tape is removed to allow the tape to anchor into tissue and fixate.

Closure—The vaginal incision can be closed with interrupted sutures but uses layering to close the perineal body incision so as to reduce potential for dyspareunia.

DETAILED DESCRIPTION OF THE INVENTION

The following description is meant to be illustrative only, and not limiting the embodiments of this invention that will be apparent to those of ordinary skill in the art in view of this description.

Figure 1:
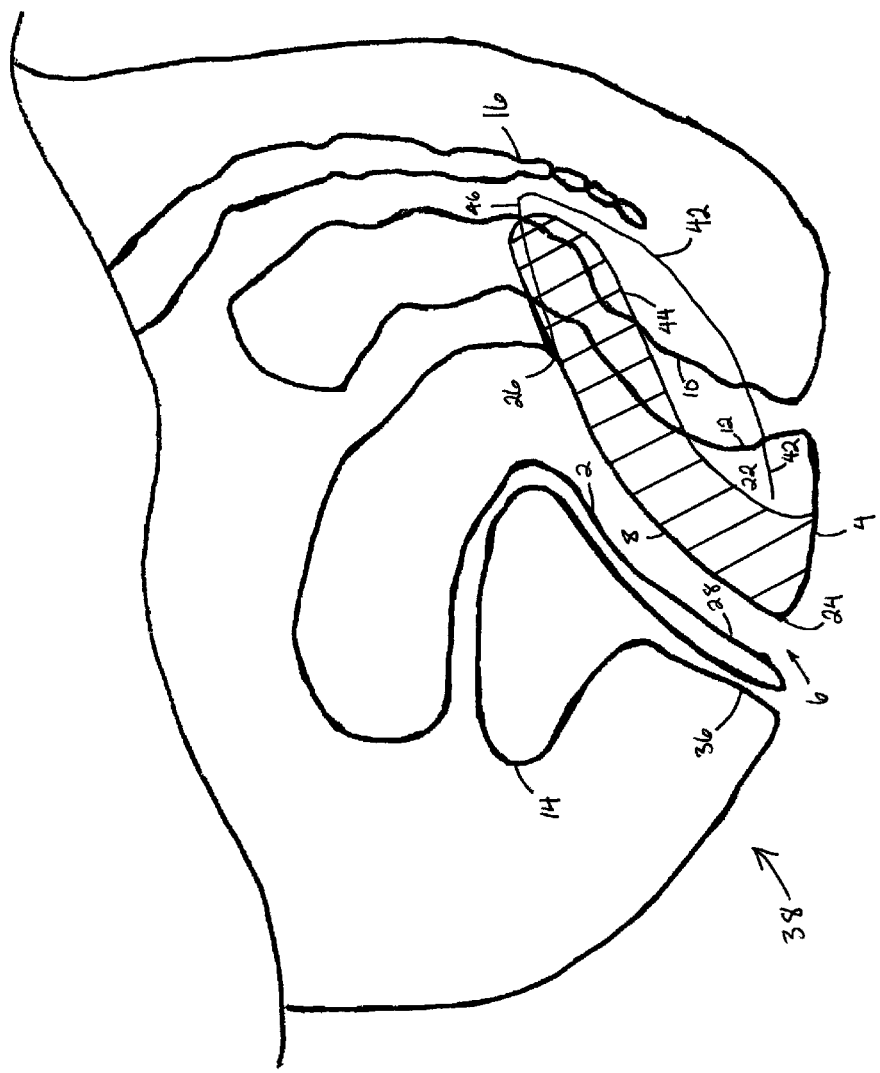
FIG. 1 is a midsagittal section view of a female pelvic region and an apical suspension according to one embodiment of the present invention.
Figure 2:
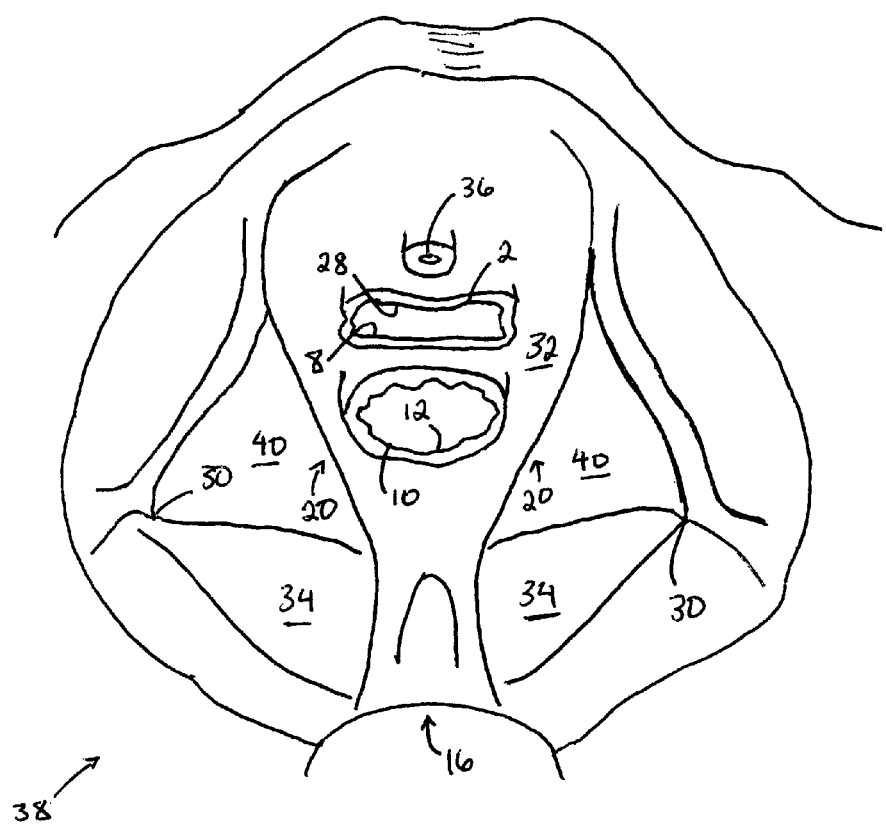
FIG. 2 is a superior view of a female pelvic diaphragm.

The invention generally involves surgical systems and methods for performing a surgical transvaginal apical suspension. In certain embodiments, the surgical procedure can include the following steps:

1. An incision is made to create an insertion tunnel 44, shown in FIG. 1 as hashed. The incision starts outside a vaginal opening 6 of a patient at a perineal body 4 and spans the entire length of a vagina 2, along a posterior vaginal wall 8. The incision is made according to known surgical techniques, for example by employing diamond or "V" shaped patterns, so as to create a straight line upon closure of the incision and return the vagina 2 to a pre-pathological state.
2. Separate out fascia of the patient, thereby allowing for the spatial orientation of a rectal wall 12 to become apparent.
3. Dissect each side of the vagina 2 of the patient in order to allow for the perirectal space to become visible and to create the insertion tunnel 44 anterior to the sacral-coccyx junction. Avoiding the cutting of a bladder 14 and a rectal wall 12 of the patient will allow for less blood in the surgical field.
6. The above-described insertion tunnel 44 (approximately 1 inch in diameter) is made with the assistance of 2 flat retractors and 1 retractor to mimic a finger retraction.
7. Once the insertion tunnel 44 is developed, the physician uses a needle or ligature carrier to create a tunnel for the mesh 42. A bioabsorbable thread or suture is then used in conjunction with the tunnel for the mesh 42 and the mesh 42 to create a pulley style system for the mesh 42.

a. The tunnel for the mesh 42 goes through and past the following musculature:
      1. Through the pubococcygeus muscle 32;
      2. Past the iliococcygeus muscle 40;
      3. Past the coccygeus muscle 34;
      4. The insertion point of the needle into the insertion tunnel 44 is ideally where the muscles start to lose definition in tendinous structure near the sacrum 16 (this will vary from patient to patient).
   b. It has been noted that almost 100 percent of vault prolapse has enterocele. This can be attributed to the lack of support by the vagina 2 on the small intestine, and this can be because enterocele is inevitable because of the additional space available after hysterectomy.

Additional steps are appropriate in accordance with the teachings of provisional application Ser. No. 61/249,511, incorporated herein by reference.

Retraction can include the use of a standalone disposal retraction system. The system would provide full access under direct visualization to the target fixation site for more effective and safe fixation.

The mesh 42 design can, for example, be the Monarc tape. Other known mesh materials or configurations, or those developed, can be used with a new weave similar to the one developed for TOPAS but would also expand to address potential requirements of a new fixation method and possibly a new way of attaching to the vaginal apex 26 and segments of the vaginal wall 8, 28.

Tissue dissection can include the development of a new method of dissection that does not entail cutting through the full length of the vaginal wall 8, 28, especially if current dissection proves to be prohibitive to some physicians.

Various systems, devices, and techniques disclosed in U.S. Pat. Nos. 7,357,773 and 7,070,556, as well as International PCT Publication Nos. WO2009/017680 and WO2009/075800, which are incorporated herein by reference in their entirety, can be used with or adapted for the surgical systems and procedures disclosed herein.

Figure 3:
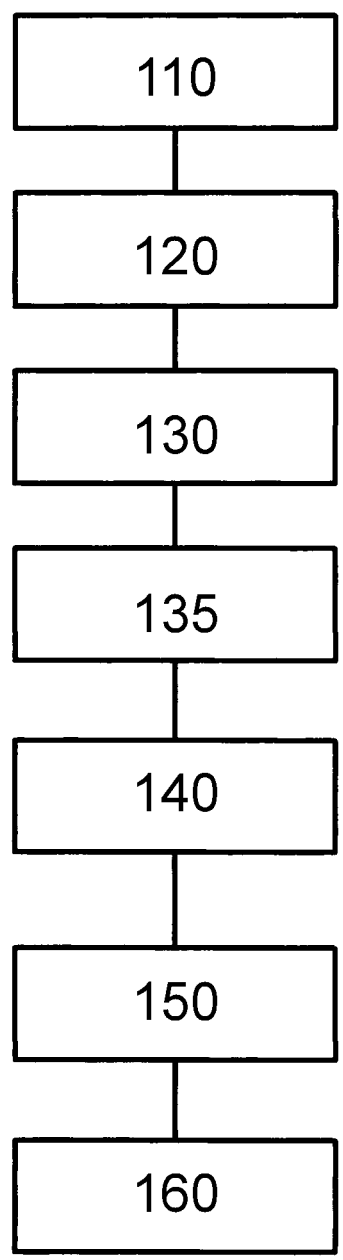
FIG. 3 is a diagram of a procedure according to one embodiment of the present invention.
Figure 4:
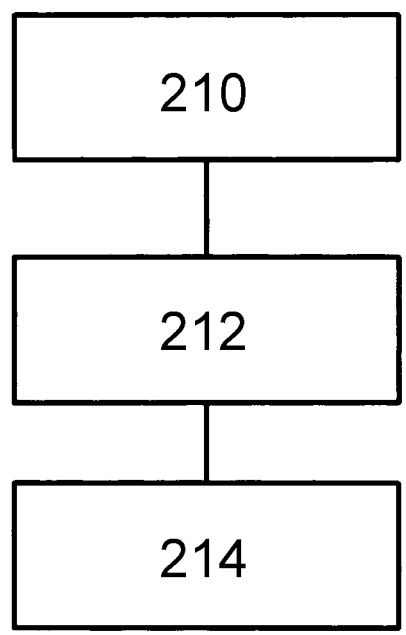
FIG. 4 is a diagram of a procedure for formation of an insertion tunnel according to one embodiment of the present invention.

Below steps a-z more particularly describe a procedure according to the present invention.

a. With reference to step 110 of FIG. 3 and step 210 of FIG. 4, the insertion tunnel 44 is formed by placing two clamps at opposing positions on each side of the vaginal opening 6 at the level of a hymen 24.
   b. A posterior incision is made in the patient starting from outside the vagina 2 at the perineal body 4 for an entire length of the vagina 2 along the posterior vaginal wall 8.
   c. With reference to step 212 of FIG. 4, the patient's skin is dissected off the perineal body 4 and a rectum 10 of the patient through the incision until the rectal-vaginal space 22 is identified.
   d. With reference to step 212 of FIG. 4, dissection is carried cephalad towards a vaginal apex 26 and the sac of the enterocele is identified.
   e. The enterocele sac is not altered and the dissection continues to the apex of the vagina 26.
   f. The dissection is then directed back towards the vaginal opening 6.
   h. With reference to step 214 of FIG. 4, the rectum 10 is mobilized medially, the para-rectal space 20 on the right is identified, and a retractor is placed to hold the bladder 14 and anterior vaginal wall 28 cephalad and the rectum 10 medially. The ischial spine 30 of the patient is visualized and palpated and the levators are noted.
   i. The dissection is continued within the para-rectal space 20 until the retro-peritoneal space is dissected as much as the patient's individual anatomy permits.
   j. With reference to step 120 of FIG. 3, a straight ligature carrier carrying a durable suture is employed to form the tunnel for the mesh 42 by puncturing through a pubococcygeus muscle 32, and advancing the needle to centimeters above the ischial spine 30 past a coccygeus (ischiococcygeus) muscle 34 above the surface of a sacrum 16 and through structure, e.g. ligamentous structure in some patients and muscular structure in others, and into the insertion tunnel 44.
   k. Usually the tunnel for the mesh 42, disclosed above instep "j", is in excess of 12 centimeters in length from the hymen 24.
   l. The suture carried by the ligature carrier is recovered with a hook inserted into the insertion tunnel 44. The suture is pulled through the anatomical structure that is at the most cephelad point of the insertion tunnel 44. The ligature carrier is removed leaving the suture that traverses through the tunnel for the mesh 42, i.e. through the coccygeus muscle 34, through all the levators, to the most cephalad point of the insertion tunnel 44, and then comes through the insertion tunnel 44.
   m. With reference to step 130 of FIG. 3, the suture of step "l" is tied to a mesh 42, for example a SPARC mesh.
   n. Should it be desired to also repair a cystocele, attention is directed anteriorly and a urethral Foley is inserted to empty the bladder 14.
   o. With reference to step 135 of FIG. 3, two Allis clamps are employed to take pinches of the anterior vaginal wall 28.
   p. An anterior incision is made into the anterior vaginal wall 28 for the full thickness of vagina 2 and the bladder 14 is separated from or off the anterior vaginal wall 28.
   q. The anterior incision described in step "p" is extended towards the apex of the vagina 26 so as to connect the anterior incision with the posterior incision described above in step "b".
   r. It is at this point that a surgeon can place a sling, for example a MiniArc sling, for repair of the cystocele.
   s. The surgeon then begins to close the anterior incision proceeding towards the apex of the vagina 26.
   t. With reference to step 140 of FIG. 3, once the apex 26 of the vagina 26 is determined, the mesh 42 is secured to the apex of the vagina 26 and the vagina 2 is elevated and repositioned back into the hollow of the pelvis 38.
   u. The opposite, free end of the suture extending out from the patient through the tunnel for the mesh 42 is then pulled or tensioned.
   v. As the suture and mesh 42 is pulled, the vagina 2 will begin to fill the dissected space until the vagina 2 is positioned at the most cephelad point by the pulley systems created by the suture and mesh 42.
   w. The plastic sheath of the mesh 42 is then pulled off the mesh 42, thereby allowing for the fixation of the mesh 42 to the patient tissue and the securing of the vaginal prolapse repair.
   x. With reference to step 150 of FIG. 3, where the surgeon has pierced the pubococcygeus muscle 32, i.e. where the mesh 42 passes through the pubococcygeus muscle 32, the mesh 42 is cut.
   y. With reference to step 160 of FIG. 3, the vaginal incisions are then closed to slightly below the level of the hymen 24.

z. The muscles of the perineal body 4 are then rebuilt and the incision over the perineal body is closed.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. A method for transvaginal apical suspension comprising:
   creating an insertion tunnel along a posterior vaginal wall for an entire length of a vagina of a patient;
   passing a first end of a suture through a pubococcygeus muscle, an iliococcygeus muscle, a coccygeus muscle, and tendinous structure near a sacrum of the patient and into the insertion tunnel;
   securing a first end of a mesh to an apex of the vagina of the patient and a second end of the mesh to the first end of the suture;
   suspending the apex of the vagina of the patient by pulling a second end of the suture;
   anchoring the mesh; and
   closing the insertion tunnel.

2. The method of claim 1 wherein the step of creating an insertion tunnel along a posterior vaginal wall for an entire length of a vagina of a patient comprises making an incision starting from outside the vagina at a perineal body of the patient.

3. The method of claim 1 wherein the step of creating an insertion tunnel along a posterior vaginal wall for an entire length of a vagina of a patient comprises dissecting skin off the patient's perineal body and exposing a rectal-vaginal space of the patient.

4. The method of claim 1 wherein the step of passing a first end of a suture through a pubococcygeus muscle, an iliococcygeus muscle, a coccygeus muscle, and tendinous structure near a sacrum of the patient and into the insertion tunnel comprises passing the suture through a levator plate of the patient.

5. The method of claim 1 wherein the step of passing a first end of a suture through a pubococcygeus muscle, an iliococcygeus muscle, a coccygeus muscle, and tendinous structure near a sacrum of the patient and into the insertion tunnel comprises passing the suture through a muscle above the surface of the sacrum of the patient.

6. The method of claim 1 wherein the step of suspending the apex of the vagina of the patient by pulling a second end of the suture comprises cutting the second end of the mesh where the mesh traverses the pubococcygeus muscle of the patient.

7. The method of claim 1 further comprising the step of making an incision in an anterior vaginal wall of the patient and repairing a cystocele.

8. A method for transvaginal apical suspension comprising:
   creating an insertion tunnel from a perineal body of a patient towards an apex of a vagina of the patient;
   attaching a first end of a mesh to the apex of the vagina of the patient;
   suspending the apex of the vagina of the patient by pulling a second end of the mesh through a ligamentous or a muscular anatomical structure of the patient near a sacrum of the patient, through an iliococcygeus muscle, through a coccygeus muscle, and through a pubococcygeus muscle of the patient;
   anchoring the mesh; and
   closing the insertion tunnel.

9. The method of claim 8 wherein the step of creating an insertion tunnel from a perineal body of a patient towards an apex of a vagina of the patient comprises making an incision starting from outside the vagina at a perineal body of the patient.

10. The method of claim 8 wherein the step of creating an insertion tunnel from a perineal body of a patient towards an apex of a vagina of the patient comprises dissecting skin off the patient's perineal body and exposing a rectal-vaginal space of the patient.

11. The method of claim 8 wherein the step of suspending the apex of the vagina of the patient by pulling a second end of the mesh through a ligamentous or a muscular anatomical structure of the patient near a sacrum of the patient, through an iliococcygeus muscle, through a coccygeus muscle, and through a pubococcygeus muscle of the patient comprises pulling the mesh through a levator plate of the patient.

12. The method of claim 8 wherein the step of suspending the apex of the vagina of the patient by pulling a second end of the mesh through a ligamentous or a muscular anatomical structure of the patient near a sacrum of the patient, through an iliococcygeus muscle, through a coccygeus muscle, and through a pubococcygeus muscle of the patient comprises pulling the mesh through a tendonous anatomical structure near the surface of the sacrum of the patient.

13. The method of claim 8 wherein the step of suspending the apex of the vagina of the patient by pulling a second end of the mesh through a ligamentous or a muscular anatomical structure of the patient near a sacrum of the patient, through an iliococcygeus muscle, through a coccygeus muscle, and through a pubococcygeus muscle of the patient comprises passing a first end of a mesh through a muscle near the surface of the sacrum of the patient.

14. The method of claim 8 wherein the step of anchoring the mesh comprises cutting the second end of the mesh where the mesh traverses the pubococcygeus muscle of the patient.

15. The method of claim 8 further comprising the step of making an incision in an anterior vaginal wall of the patient and repairing a cystocele.

\* \* \* \* \*